United States Patent
Cawthorne et al.

(12) 
(10) Patent No.: US 6,420,578 B1
(45) Date of Patent: *Jul. 16, 2002

(54) WOOLGREASE

(75) Inventors: Richard Neil Cawthorne, North Yorkshire; Robert William Humble, East Yorkshire; David Andrew Parker, Hull, all of (GB)

(73) Assignee: Croda International PLC, North Humberside (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,328

(22) Filed: Jul. 16, 1999

(51) Int. Cl.$^7$ .................................................. C11B 3/00
(52) U.S. Cl. ........................ 554/195; 554/156; 554/201
(58) Field of Search ................................ 554/174, 175, 554/177, 213, 156, 195, 201; 552/545; 508/451; 514/558, 943; 424/401

(56) References Cited

U.S. PATENT DOCUMENTS 5,155,245 A * 10/1992 Myojo et al. ................ 552/545
5,556,970 A * 9/1996 Kawasaki et al. .......... 554/190

FOREIGN PATENT DOCUMENTS

| EP | 0129014 | 12/1984 | | |
|----|---------|---------|---|---|
| EP | 0596135 | 5/1994 | | |
| EP | 0682935 | 11/1995 | | |
| EP | 0705604 | 4/1996 | | |
| WO | WO 98/30532 | * 7/1998 | .......... | A61K/59/01 |

OTHER PUBLICATIONS

Database WPI, Section Ch, Week 9248, Derwent Publications Ltd.
Patent Abstracts of Japan, vol. 012, No. 297, Aug. 12, 1988.
Patent Abstracts of Japan, vol. 016, No. 461, Sep. 25, 1992.
A. Korner et al: The fatty acid composition of lipids from the wool cell membrane complex, vol. 344, pp. 501–509.

* cited by examiner

*Primary Examiner*—Deborah D. Carr
(74) *Attorney, Agent, or Firm*—Stevens, Davis, Miller & Mosher, LLP

(57) ABSTRACT

A process for recovering 18-methyl eicosanoic acid (18-MEA) and/or alpha hydroxy acids (AHAs) from woolwax acids or derivatives thereof comprises the steps of heating the woolwax acids or derivatives thereof to 100 to 230° C. to form estolides and polymeric species; distilling to obtain a distillate (D1) and a residue (R1); and recovering 18-MEA from the distillate and/or recovering AHAs from the residue.

42 Claims, No Drawings

WOOLGREASE

This invention relates to a process for recovering 18-methyl eicosanoic acid (18-MEA) and/or alpha hydroxy acids from woolwax acids or derivatives thereof. These materials can be employed as active ingredients in personal care products.

By "alpha hydroxy acids", we mean acids of the formula:

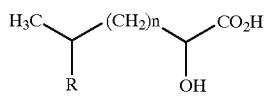

where R can be $CH_3$ or H and n is in the range 10 to 22.

The formula of 18-MEA is:

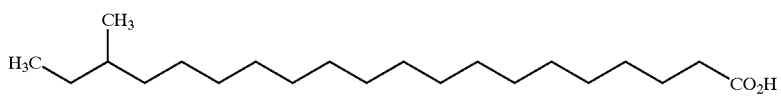

Woolwax is the preferred name for the fat or grease found in the wool of sheep, Ovis aries. In its virgin unrefined state it is one of the best preventatives for rust, but generally woolwax is refined by chemical processing into commercially useful materials in one of two ways. Firstly, it is purified by a refining procedure to give Lanolin. Lanolin is the refined version of woolwax and is used primarily in a hydrated version as an emollient to soothe, smooth and calm dry or damaged skin. Secondly, the woolwax can be saponified to provide separate alcohol and acid fractions. The alcohol fraction is a complex mixture of sterols and fatty alcohols. This fraction has numerous uses, primarily to give emollient and emulsification properties to products in the personal care industry. By contrast, however, the woolwax acid fraction, although utilised to some extent in the personal care industry, has not found the same number of end user markets. This may in part be due to the highly complex nature of the fatty acids within the woolwax acid fraction which would by convention be considered as an impure source of fatty acids when compared to the use of oil seed triglycerides or tallow. Woolwax acids have a complex lipid profile consisting of iso, ante-iso and normal fatty acids and iso and nonnal alpha hydroxy fatty acids having carbon backbone skeletons ranging in carbon chain length from eight to thirty carbon atoms. More specifically the iso and normal alpha hydroxy fatty acid carbon backbone skeletons range in carbon chain length from fourteen to twenty six carbon atoms. Table 1.0 (hereinafter) shows the typical fatty acid groups within the woolwax acid lipid profile and also indicates the typical total levels of these groups within the said profile. The most abundant fatty acid within the woolwax acid composition is alpha hydroxy palmitic acid which ranges from 10% w/w to 16% w/w and, more particularly, 11% w/w to 14% w/w.

As the understanding of cosmetic ingredients and their potential modes of action have advanced, a market requirement has developed for specifically purified fractions of the woolwax acids. For example, the alpha hydroxy acid (AHA) components are believed to reduce the symptoms of skin ageing that result from sun exposure and other environmental factors. The effects of the AHA's within an emollient based cream are met with reductions in the following symptoms, mottled hyperpigmentation, fine and course wrinkling, laxity, sallowness, telangiectasia and tactile roughness. The AHA product is believed to exhibit these improvement qualities only when correctly formulated. In the case of reducing skin roughness, for example, the mode of action is by limiting the degree of transepidermal water loss.

Contained within the ante-iso fatty acid homologues of the woolwax acid fraction is the important lipid 18-MEA. This is a major structural lipid found as the major fatty acid species within the hair lipid matrix of mammalian hair (D. J. Fleet, R. E. H. Wettenhall, D. E. Rivett and A. K. Allen; A comparative study of covalently-bound fatty acids in keratinized tissues, Comp. Biochem. Physiol, Vol 102B, No.2, 363–366, (1992). This ante-iso fatty acid has been demonstrated as the active ingredient when formulated within hair care products. 18-MEA is also found as part of the wax ester matrix which makes up Woolwax. The long chain ante-iso fatty acid is typically found at levels of 1% w/w to 4% w/w of the woolwax acids, though more usually at levels of 2% w/w to 3.5 w/w.

Because of the commercial interest in 18-MEA and the AHA's, efforts have been made to obtain purified versions of these materials. For example, the isolation of AHA's from woolwax and woolwax acids has been attempted using various approaches eg. transit metal chelation (A. H. Milburn and E. V. Truter, Extraction of 2-hydroxy acids from Wool Wax Acids, J. Appl. Chem; 12, 156–160 (1962) and solvent fractionation (Downing, Solvent Fractionation of Wool Wax Acids, Aust. J Appl. Sci., 14 (No. 1) 50–56, (1962), and Beiersdorf A G, EP-A-555776).

A complicating factor in the separation of AHA's from woolwax and woolwax acids is the thermal instability of the AHA moiety due to the presence of the hydroxyl functionality in the alpha position which not increase the acidity of the carboxylic acid group but also gives a centre for further side reactions. This thermal lability results in the formation of lactones/estolides and polymers. The net result of these reactions means that the woolwax acid has a significant reduction in the total amount of AHA that can be recovered. This degradation is well documented (see for example W. R. Noble, A. Eisner and J. T. Scanlan, isolation of a Hydroxy Acid Concentrate from Wool Wax Acids, JAOCS, 37, 14–16, (1960)).

As far as 18-MEA is concerned, the concentration of this component in woolwax acid is fairly low, typically in the range of 1 to 4% w/w and more specifically 2.5 to 3.5% w/w. These variations are accounted for according to the geographical location of the raw material and the breed of sheep from which the woolwax was scoured. It would also appear that little work has been carried out for the isolation of this material from woolwax. Work has been done to isolate the integral 18-MEA from the hair lipid matrix of mammalian hair but, this is not a commercial route since it does not permit the recovery of large enough quantities of the acid for the personal care market. Attempts have been made to synthesise 18-MEA but, in general, these involve complex multistep processes which inevitably result in low yielding routes to the desired product. The synthetic material also faces the problem of being accepted within the personal care sector as it has not been derived from a natural source which automatically places it at a disadvantage.

It is therefore, highly desirable to achieve a cost effective and robust process to isolate both an AHA enriched and an 18-MEA enriched lipid blend directly from woolwax acids.

According to the present invention, there is provided a process for recovering 18-methyl eicosanoic acid (18-MEA) and/or alphahydroxy acids from woolwax acids or derivatives thereof, which comprises heating the woolwax acids or derivatives thereof to 100° to 230° C. to form estolides and polymeric species; distilling to obtain a distillate and a residue; and recovering 18-MEA from the distillate and/or recovering alpha hydroxy acids from the residue.

The process of the invention surprisingly relies for its selectivity on the ability of the AHA's to form the estolide and polymeric species. This has hitherto been seen as an undesirable feature in the isolation of AHA's from woolwax.

The preferred feedstock of the invention is the woolwax acids as obtained from saponification of woolwax, but certain derivatives of woolwax acids can also be used as the feedstock for this invention, provided that the derivatives form estolides and polymers upon heat treatment. Suitable derivatives would be esters involving the acid functionality of the woolwax and/or esters of the hydroxyl functionality of the AHA's. Examples of suitable derivatives would include methyl, ethyl and propyl esters of the woolwax fatty acids, and formates and acetates of the AHA's within the woolwax acid mixtures. Preferably, woolwax acids are used as this involves fewer processing steps and in this way gives the 18-MEA concentrate in the more desirable free acid form. The form of the AHA has no consequence as the saponification step hydrolyses directly to the free fatty acid.

In the process of the invention, the woolwax acid (or derivatives) feedstock is heated to 100° C. to 230° C., preferably 150° C. to 200° C., most preferably 160° C. to 180° C. The heating is generally maintained for about 1 to 48 hours, preferably 3 to 16 hours, and most preferably 5 to 10 hours. A vacuum can be used to displace the equilibrium towards estolide/polymer formation. A catalyst may be used at this stage but we have found that the reaction will proceed well uncatalysed. If a catalyst is used, however, then conventional esterification catalysts such as sodium hydroxide, sodium methoxide, sodium ethoxide, potassium hydroxide, potassium tert-butoxide, mineral acids like phosphorus acids, for example phosphoric acid or hypophosphorus acid, sulphuric acid, hydrochloric acid, and organic acids like methane sulphonic acid and p-toluene sulphoric acid, are suitable. These catalysts are merely examples as will be appreciated by those skilled in the art, and any suitable material that speeds up the desired reaction may be employed for the purposes of catalysing the reaction, providing the desired final polymeric material is prepared.

Following the interesterification reaction, the product is distilled under vacuum, preferably less than $1 \times 10^{-1}$ mbar and most preferably less than $1 \times 10^{-2}$ mbar, at a temperature of between 150° and 250° C. to yield a distillate (D1) depleted in AHA's and a residue (R1) comprising essentially interesterified AHA's. The distillation can be a separate stage or a direct stage. The separate procedure is described in full below and an example of a direct procedure is given in the Examples. The interesterification and total distillation can be achieved in a vessel capable of handling vacuums of the level described.

Following the distillation, the AHA's may be recovered from the residue (R1). Thus, for example, the residue may be saponified to yield the fatty acid soaps of the AHA's. This saponification can, for example, be carried out using an alcoholic solution of an appropriate base, for example sodium or potassium hydroxide, in water but it will be appreciated by those skilled in the art that other conditions can equally be used. The soaps may then be purified such as by solvent extraction. We have used n-hexane to extract the unsaponifiable components from the aqueous alcoholic solution of the soaps but it will be appreciated that any solvent which is immiscible with the aqueous alcoholic phase and has sufficient solubility for the unsaponifiable by-products, can be used. Examples include, for example, petroleum ether 40/60 bp., petroleum ether 60/80 bp and diethylether. The purified soaps can then be acidified to regenerate the free fatty acid. The types of acid that can be used for the purposes of hydrolysing the soaps are not limited to the more common mineral acids, for example hydrochloric acid and sulphuric acids, but as will be appreciated by those skilled in the art, any strong acid can be used either as a solution or as a bound acid, for example an ion exchange resin.

The free AHA concentrate thus obtained may be further purified by distillation under vacuum, preferably less than $1 \times 10^{-1}$ mbar and most preferably less than $1 \times 10^{-2}$ mbar, at a temperature of between 100° C. and 230° C., preferably between 110° and 200° C. and most preferably between 120° C. and 180° C., to yield a distillate (D2) elevated in AHA's and a residue (R2) essentially comprising high molecular weight fatty acids and some interesterified AHA's. The concentration of AHA's in the purified product (D2) will depend on the concentration of AHA's within the original raw material woolwax acids which is itself a natural product and will of course be variable. However, typically we would expect the ratio of AHA% in the purified product to AHA% in the raw material, to be in the range of about 1.1 to 3.0, more preferably 1.3 to 2.5, and most preferably 1.7 to 2.2.

The 18-MEA lipid fraction can be derived by processing the distillate (D1) in a number of different ways. We prefer to use either distillation, urea inclusion complexation or chromatographic refining, or a combination of the three processes to obtain the desired 18-MEA level within the final concentrate. Our preferred route is that of distillation followed by chromatographic-refining as this has less environmental impact with respect to the disposal of the waste inclusion complex, namely the urea and waste fatty acid. If an inclusion complex agent is to be used, it must be appreciated by those skilled in the art that any conventional inclusion forming complex agent can be used under appropriate conditions.

The distillate (D1) obtained as described above may be further purified b distillation under vacuum preferably less than $1 \times 10^{-1}$ mbar and most preferably less than $1 \times 10^{-2}$ mbar at a temperature of between 100° C. and 230° C., preferably between 110° C. and 200° C. and most preferably between 120° C. and 180° C., to yield a distillate (D3) elevated in 18-MEA and a residue (R3) comprised essentially of higher molecular weight fatty acids and low levels of interesterified AHA's. Clearly, the concentration of 18-MEA in the purified product (D3) will depend on the concentration of 18-MEA within the original raw material woolwax acids which is itself a natural product and will of course be variable. However, typically we would expect the ratio of 18-MEA% in the purified product to 18-MEA % in the raw material, to be in the range of about 1.1 to 1.5.

The distillate (D3) thus obtained may be further purified by distillation under vacuum, preferably less than $1 \times 10^{-1}$ mbar and most preferably less than $1 \times 10^{-2}$ mbar, at a temperature of between 80° C. and 230° C., preferably between 95° C. and 190° C. and most preferably between 105° C. and 160° C., to yield a distillate (D4) depleted in 18-MEA and a residue (R4) comprising an elevated level of 18-MEA. Clearly the amount of 18-MEA in the purified residue (R4) will depend on the concentration of 18-MEA within the previous distillate (D3) which will also be affected by the concentration of 18-MEA within raw material woolwax acids which is itself a natural product and will of course be variable. However, typically we would expect the ratio of 18-MEA % in the purified residue (R4) to 18-MEA % in the raw material, to be in the range of about 1.0 to 10.0, more specifically in the range 2.0 to 5.0. It will also be appreciated that the distillation conditions can be altered in any combination and are not limiting. For example conditions can be used where the residue (R3) contains the elevated levels of 18-MEA and then the distillate (D4) also has elevated levels of 18-MEA.

Any 18-MEA concentrate can be chromatographically refined to give a desired product specification. Usually the 18-MEA fatty acid concentrate is solubilised in an appropriate solvent. One suitable solvent is n-hexane but it will be appreciated that any solvent which is miscible with the fatty acid with sufficient solubility power will be suitable, for example petroleum ether 40/60 bp., petroleum ether 60/80 bp or diethylether, can be used. In our process, we prefer to dissolve about 1 part fatty acid in about 1 part solvent, though the degree of solute concentration within solvent is not critical. The process can be performed at any temperature provided a complete solution is maintained. If the solution is to be heated, it is preferably performed safely at the appropriate temperature below the boiling point of the solvent. The fatty acid solution is then passed through an appropriate inert absorbent earth to remove the odour bodies, colour bodies and polar species from the solution. The amount of earth that is used depends on the degree of colour improvement or, odour removal that is required. Typically the ratio of fatty acid used to earth used is in the range of about 0.5 to 4.0, preferably 0.9 to 2.0 and most preferably 1.0 to 1.5. This process can also be used to further concentrate the 18-MEA which depends to some extent on the ratio of fatty acid used to earth used, which dictates how much material is absorbed onto the earth. For example, if 8% of polar fatty acids are totally removed by the earth from the original fatty acid mixture, the level of 18-MEA will be further elevated by 8% W/W.

The distillates (D1 and D3) and residue (R4) may be further purified by removing the normal saturated fatty acids by formation of inclusion complexation from the fatty acid mixtures. We prefer to use urea as the inclusion complex forming agent and industrial methylated spirits as the solvent, but it will be appreciated by those skilled in the art that these conditions/reagents are not critical. Typically the ratio of urea to industrial methylated spirits is in the range of 1 to 10, preferably 2 to 8 and most preferably 3 to 5. The ratio of distillates (D1 or D3) or residue (R4) to urea is also not critical and typically the range is about 0.25 to 10, preferably 0.75 to 4 and most preferably 1 to 3.

In a further aspect of the invention there is provided a cosmetic product containing 18-MEA or an AHA produced according to the process of the present invention. The cosmetic product may be included in compositions for hair treatment, such as shampoos, conditioners, permanent waves, or for skin treatment, for example creams, lotions, serums and make-up.

In order that the invention may be more fully understood, the following Examples are given by way of illustration only.

EXAMPLE 1

Interesterification and Direct Distillation of Woolwax Acids

A feedstock of woolwax acids (8.0 g, acid value 127.8 mg KOH $g^{-1}$) was stirred and heated to 170° C. under a full vacuum (1 mbar) for 3 hours in a Kugelrohr laboratory distillation unit with a three bulb set-up. After this time, the temperature was increased to 230° C. for the distillation. After 2 hours, the apparatus was cooled to give a brown waxy residue (3.0 g, 37.5% w/w acid value 40.0 mg KOH $g^{-1}$) and an amber solid distillate (5.0 g, 62.5% w/w, 198.0 mg KOH $g^{-1}$). The fatty acid compositions were determined as follows: The non-esterified products, that is those having been prepared as distillates or hydrolysed fatty acids, were refluxed briefly with the appropriate quantity of N-O-bis-(trimethylsilyl)trifluoroacetamide followed by gas chromatographic analysis.

The interesterified products, that is those prepared as polymeric materials, were initially saponified to their corresponding soaps, hydrolysed to the free fatty acid and refluxed briefly with the appropriate quantity of N-O-bis-(trimethylsilyl)trifluoroacetamide, followed by gas chromatographic analysis. The fatty acid compositions for the residue and distillate are shown in tables 2.0 and 3.0, respectively.

EXAMPLE 2

Interesterification of Woolwax Acids

A feedstock of woolwax acids (3000.0 g, acid value 127.8 mg KOH $g^{-1}$) was stirred and heated to 170° C. under a full vacuum (1 mbar) for 6 hours. After this time, the polymerised product was cooled to room temperature to give a brown waxy solid (2970.0 g, 99.0% w/w, acid value 78.6 mg KOH $g^{-1}$).

EXAMPLE 3

Distillation of Interesterified Woolwax Acids

The interesterified woolwax acids (1776.4 g) were distilled on a CD-6 thin film evaporator under the following conditions;

| | |
|---|---|
| Feed | 1776.4 g |
| Evaporator | 205° C. |
| Condenser | 70° C. |
| Vacuum | $4 \times 10^{-3}$ mbar |
| Feed rate | 6/8 ml $min^{-1}$ |
| Wiper speed | 7 |
| Distillate (D1) | 693.1 g (Table 4.0) |
| Residue (R1) | 1073.3 g |
| Losses | 10.0 g |

EXAMPLE 4

Saponification and Extraction of the Interesterified Woolwax Acid Residue (R1)

The distilled interesterified woolwax acid residue ((R1), 15.0 g), industrial methylated spirits (50 ml), distilled water (25 ml) and potassium hydroxide (2.0 g) were refluxed for 1 hour. After this time, the reaction mixture was cooled to approximately 50° C. and diluted with more distilled water (15 ml). This solution was extracted with diethylether (3×10 ml) to remove the unsaponifiable material.

The ethereal phase was washed with dilute aqueous potassium hydroxide ((2% w/w KOH in cold distilled water), 2×5 ml). The aqueous phases were combined and acidified to pH1 with cold dilute aqueous hydrochloric acid (10% v/v) and extracted with diethylether (3×10 ml), washed to neutrality with cold distilled water and dried over anhydrous sodium sulphate. The resulting solution was filtered and evaporated under vacuum to dryness to yield a brown waxy solid, (12.5 g, 83.3% w/w).

Table 5.0 shows the lipid profile for the saponified/hydrolysed enhanced AHA product.

EXAMPLE 5

Saponification and Extraction of the Interesterified Woolwax Acid Residue (R1)

The distilled interesterified woolwax acid residue ((R1), 15.0 g), industrial methylated spirits (50 ml), distilled water (25 ml) and potassium hydroxide (2.0 g) were refluxed for 5 hours. After this time, the reaction mixture was cooled to approximately 50° C. and diluted with more distilled water (15 ml). This solution was extracted with diethylether (3×10 ml) to remove the unsaponifiable material.

The ethereal phase was washed with dilute aqueous potassium hydroxide ((2% w/w KOH in cold distilled water), 2×5 ml). The aqueous phases were combined and acidified to pH1 with cold dilute aqueous hydrochloric acid (10% v/v) and extracted with diethylether (3×10 ml), washed to neutrality with cold distilled water and dried over anhydrous sodium sulphate. The resulting solution was filtered and evaporated under vacuum to dryness to yield a brown waxy solid (12.0 g, 80.0% w/w).

Table 6.0 shows the lipid profile for the saponified/hydrolysed enhanced AHA product.

EXAMPLE 6

Saponification and Extraction of the Interesterified Woolwax Acid Residue (R1)

The distilled interesterified woolwax acids residue ((R1), 583.0 g), industrial methylated spirits (500 ml), distilled water (500 ml) and potassium hydroxide (90 g) were stirred under reflux for 5 hours. After this time, the reaction mixture was cooled to approximately 50° C. and diluted with more distilled water (1000 ml). This solution was passed through a counter current of n-hexane (3×1000 ml) at 55° C. to extract the unsaponifiable material.

The aqueous phase was acidified with dilute hydrochloric acid (1000 ml of 10% v/v) and stirred for 40 minutes to afford complete hydrolysis. The free fatty acids were then extracted in warm n-hexane (2000 ml, 40° C.) and washed to neutrality with aqueous isopropylalcohol (5×500 ml, 30% v/v IPA in water).

Finally, the free fatty acids were evaporated to dryness under reduced pressure at 80° C. for 40 minutes and then cooled to room temperature to give a brown waxy solid (480.0 g, 82.0% w/w).

Table 7.0 shows the lipid profile for the saponified/hydrolysed enhanced AHA product.

EXAMPLE 7

Distillation of Hydrolysed Interesterified Woolwax Acids

The hydrolysed interesterified woolwax acids (from Example 4 above) were finally distilled on a CD-6 thin film evaporator to give the final distillate (D2) and a residue (R2) under the following conditions:

| | |
|---|---|
| Feed | 411.0 g |
| Evaporator | 165° C. |
| Condenser | 75° C. |
| Vacuum | $5 \times 10^{-3}$ mbar |
| Feed rate | 6/8 ml min$^{-1}$ |
| Wiper speed | 7 |
| Distillate (D2) | 238.8 g (Table 8.0) |
| Residue (R2) | 162.8 g (Table 9.0) |
| Losses | 9.4 g |

The final distillate (D2) had the following analysis:

| | |
|---|---|
| Colour (Gardner) | 5 |
| Acid Value | 166.0 mg KOH g$^{-1}$ |
| Saponification Value | 166.5 mg KOH g$^{-1}$ |
| Iodine Value | 7.4 |
| Moisture | <0.1% w/w |
| Slip Point | 58.6° C. |

The fatty acids compositions for the distillate (D2) and the residue (R2) are shown in tables 8.0 and 9.0 respectively.

EXAMPLE 8

Distillation of Distillate (D1)

The interesterified woolwax acid distillate (D1) was re-distilled on a CD-6 thin film evaporator to give a distillate (D3) and residue (R3) under the following conditions;

| | |
|---|---|
| Feed | 237 g |
| Evaporator | 150° C. |
| Condenser | 70° C. |
| Vacuum | $3.5 \times 10^{-2}$ mbar |
| Feed rate | 6/8 ml min$^{-1}$ |
| Wiper speed | 7 |
| Distillate (D3) | 142.5 g (Table 10.0) |
| Residue (R3) | 84.0 g (Table 11.0) |
| Losses | 6.5 g |

The fatty acid compositions for the distillates (D1) and (D3) and the residue (R3) are shown in Tables 4.0, 10.0 and 11.0 respectively.

EXAMPLE 9

Re-distillation of Distillate (D3)

The distillate (D3) was re-distilled on a CD-6 thin film evaporator to give a new distillate (D4) and residue (R4) under the following conditions;

| | |
|---|---|
| Feed | 138.9 g |
| Evaporator | 115° C. |
| Condenser | 65° C. |
| Vacuum | $3.5 \times 10^{-2}$ mbar |
| Feed rate | 6/8 ml min$^{-1}$ |
| Wiper speed | 7 |
| Distillate (D4) | 77.3 g (Table 10.0) |
| Residue (R4) | 55.1 g (Table 11.0) |
| Losses | 6.5 g |

The fatty acid compositions for the distillate (D4) and the residue (R4) are shown in tables 12.0 and 13.0 respectively.

EXAMPLE 10

Chromatographic Refining Residue (R4)

The residue [(R4), 30.0 g], was dissolved in n-hexane (30 ml) and passed through tonsil earth (45.0 g) at 40° C. The column was cleared with 2.5 column volumes of n-hexane. The solution was evaporated to dryness and finally stripped free of residual n-hexane under a full vacuum (<1 mm Hg) at 70° C. for 3 hours to give a pale yellow oil which solidified to give a pale yellow waxy solid, (25.35 g), 84.5%). The final super-refined product had the following analysis:

| | |
|---|---|
| Colour (Gardner) | 4 |
| Acid Value | 155.7 mg KOH g$^{-1}$ |
| Saponification Value | 159.0 mg KOH g$^{-1}$ |
| Moisture | <0.1% w/w |
| Slip Point | 51.0° C. |

The fatty acid profile for this product is given in Table 14.0.

EXAMPLE 11

Chromatographic Refining Distillate (D1)

The distillate [(D1), 17.0 g] was dissolved in n-hexane (30 ml) and passed through tonsil earth (17.0 g) at room temperature. The column was cleared with 3.0 column volumes of n-hexane. The solution was evaporated to dryness and finally stripped free of residual n-hexane under a full vacuum (<1 mm Hg) at 70° C. for 3 hours to give a pale yellow oil which solidified to give a pale yellow waxy solid, (11.0 g, 64.7%).

The fatty acid profile for this product is given in Table 15.0.

EXAMPLE 12

Urea Inclusion Complexation of Distillate (D1)

The distillate ((D1), 10.0 g), urea (15.0 g) and industrial methylated spirit (60 ml) were stirred under reflux for 2 hours and then cooled to room temperature with stirring overnight. The resulting inclusion complex (clathrate) was removed by filtration and set aside and the supernatant evaporated to dryness under vacuum. The evaporated residue (non-clathrate) was taken up in n-hexane (75 ml) washed with dilute phosphoric acid (0.5% w/w, 100 ml), then washed to neutrality with cold distilled water and dried over anhydrous sodium sulphate. The resulting solution was filtered and evaporated under vacuum to dryness to yield an amber waxy solid (4.6 g, 46.0% w/w).

The fatty acid composition for this non-clathratable product is given in table 16.0, see below;

The clathrate was diluted with water and adjusted to pH1 with cold concentrated hydrochloric acid. This mixture was extracted with n-hexane (2×30 ml) washed with dilute phosphoric acid (0.5% w/w, 100 ml), then washed to neutrality with cold distilled water and dried over anhydrous sodium sulphate. The resulting solution was filtered and evaporated under vacuum to dryness to yield an amber waxy solid, (2.5 g, 25.0% w/w).

The fatty acid composition for this clathratable product is given in Table 17.0.

EXAMPLE 13

Urea Inclusion Complexation of Distillate (D1)

The distillate ((D1), 10.0 g), urea (6.0 g) and industrial methylated spirits (24 ml) were stirred under reflux for 2 hours and then cooled to room temperature with stirring overnight. The resulting inclusion complex was removed by filtration and set aside and the supernatant evaporated to dryness under vacuum. The evaporated residue was taken up in n-hexane (75 ml) washed with dilute phosphoric acid (0.5% w/w, 100 ml), then washed to neutrality with cold distilled water and dried over anhydrous sodium sulphate. The resulting solution was filtered and evaporated under vacuum to dryness to yield an amber waxy solid, (5.4 g, 54.0% w/w).

The fatty acid composition for this non-clathratable product is given in Table 18.0.

The clathrate was diluted with water and adjusted to pH1 with cold concentrated hydrochloric acid. This mixture was extracted with n-hexane (2×30 ml) washed with dilute phosphoric acid (0.5% w/w, 100 ml), then washed to neutrality with cold distilled water and dried over anhydrous sodium sulphate. The resulting solution was filtered and evaporated under vacuum to dryness to yield an amber waxy solid, (2.1 g, 21.0% w/w).

The fatty acid composition for this clathratable product is given in Table 19.0.

EXAMPLE 14

Urea Inclusion Complexation of Distillate (D1)

The distillate ((D1), 10.0 g), urea (10.0 g) and industrial methylated spirits (40 ml) were stirred under reflux for 2 hours and then cooled to room temperature with stirring overnight. The resulting inclusion complex was removed by filtration and set aside and the supernatant evaporated to dryness under vacuum. The evaporated residue was taken up in n-hexane (75 ml) washed with dilute phosphoric acid (0.5% w/w, 100 ml), then washed to neutrality with cold distilled water and dried over anhydrous sodium sulphate. The resulting solution was filtered and evaporated under vacuum to dryness to yield an amber waxy solid, (5.0 g, 50.0% w/w).

The fatty acid composition for this non-clathratable product is given in Table 20.0.

The clathrate was diluted with water and adjusted to pH1 with cold concentrated hydrochloric acid. This mixture was extracted with n-hexane (2×30 ml) washed with dilute phosphoric acid (0.5% w/w, 100 ml), then washed to neutrality with cold distilled water and dried over anhydrous sodium sulphate. The resulting solution was filtered and evaporated under vacuum to dryness to yield an amber waxy solid, (2.2 g, 22.0% w/w)

The fatty acid composition for this clathratable product is given in Table 21.0.

The following Tables have been referred to hereinabove.

TABLE 1.0

| Typcial fatty acid composition of woolwax acids. | |
|---|---|
| Lipid Profiles | /% w/w |
| a C11 to a C19 | 12.9 |
| a C21 | 3.6 |
| a C23 to a C29 | 9.5 |
| Group Total | 26.0 |
| n C10 to n C30 | 14.8 |

TABLE 1.0-continued

Typcial fatty acid composition of woolwax acids.

| Lipid Profiles | /% w/w |
|---|---|
| Group Total | 14.8 |
| i C10 to i C28 | 23.3 |
| Group Total | 23.3 |
| C14 OH to C24 OH | 11.4 |
| n C16 OH | 14.0 |
| Group Total | 25.4 |
| Higher molecular Weight/Unknowns | 10.5 |
| Grand Total | 100.0 |

TABLE 2.0

Fatty Acid Composition The Residue (Example 1).

| Lipid Profiles | /% w/w |
|---|---|
| a C11 to a C19 | 6.8 |
| a C21 | 2.1 |
| a C23 to a C29 | 10.0 |
| Group Total | 18.9 |
| n C10 to n C30 | 10.6 |
| Group Total | 10.6 |
| i C10 to i C28 | 17.5 |
| Group Total | 17.5 |
| C14 OH to C24 OH | 21.0 |
| n C16 OH | 23.3 |
| Group Total | 42.3 |
| Higher molecular Weight/Unknowns | 10.7 |
| Grand Total | 100.0 |

TABLE 3.0

Fatty Acid Composition The Distillate (Example 1).

| Lipid Profiles | /% w/w |
|---|---|
| a C11 to a C19 | 26.1 |
| a C21 | 3.1 |
| a C23 to a C29 | 2.1 |
| Group Total | 31.3 |
| n C10 to n C30 | 20.3 |
| Group Total | 20.3 |
| i C10 to i C28 | 31.2 |
| Group Total | 31.2 |
| C14 OH to C24 OH | 5.2 |
| n C16 OH | 6.4 |
| Group Total | 11.6 |
| Higher molecular Weight/Unknowns | 5.6 |
| Grand Total | 100.0 |

TABLE 4.0

Fatty Acid Composition of Distillate (D1) (Example 3).

| Lipid Profiles | /% w/w |
|---|---|
| a C11 to a C19 | 15.9 |
| a C21 | 4.4 |
| a C23 to a C29 | 13.5 |
| Group Total | 33.8 |
| n C10 to n C30 | 22.5 |
| Group Total | 22.5 |
| i C10 to i C28 | 31.4 |
| Group Total | 31.4 |
| C14 OH to C24 OH | 6.2 |
| n C16 OH | 2.9 |
| Group Total | 9.3 |
| Higher molecular Weight/Unknowns | 3.0 |
| Grand Total | 100.0 |

TABLE 5.0

Fatty Acid Composition of The Residue After 1 Hour Saponification (Example 4).

| Lipid Profiles | /% w/w |
|---|---|
| a C11 to a C19 | 5.7 |
| a C21 | 2.0 |
| a C23 to a C29 | 5.0 |
| Group Total | 12.7 |
| n C10 to n C30 | 6.3 |
| Group Total | 6.3 |
| i C10 to i C28 | 9.4 |
| Group Total | 9.4 |
| C14 OH to C24 OH | 23.6 |
| n C16 OH | 29.0 |
| Group Total | 52.6 |
| Higher molecular Weight/Unknowns | 19.0 |
| Grand Total | 100.0 |

TABLE 6.0

Fatty Acid Composition of The Residue After 5 Hours Saponification (Example 5).

| Lipid Profiles | /% w/w |
|---|---|
| a C11 to a C19 | 8.8 |
| a C21 | 2.5 |
| a C23 to a C29 | 6.2 |
| Group Total | 17.5 |
| n C10 to n C30 | 9.8 |
| Group Total | 9.8 |
| i C10 to i C28 | 14.9 |
| Group Total | 14.9 |
| C14 OH to C24 OH | 22.3 |
| n C16 OH | 27.4 |

TABLE 6.0-continued

Fatty Acid Composition of The Residue After 5 Hours Saponification (Example 5).

| Lipid Profiles | /% w/w |
|---|---|
| Group Total Higher molecular Weight/Unknowns | 49.7 8.1 |
| Grand Total | 100.0 |

TABLE 7.0

Fatty Acid Composition of The Saponified Residue (R1) (Example 6)

| Lipid Profiles | /% w/w |
|---|---|
| a C11 to a C19 | 6.2 |
| a C21 | 2.2 |
| a C23 to a C29 | 6.0 |
| Group Total n C10 to n C30 | 14.4 8.4 |
| Group Total i C10 to i C28 | 8.4 11.7 |
| Group Total C14 OH to C24 OH n C16 OH | 11.7 16.2 21.8 |
| Group Total Higher molecular Weight/Unknowns | 37.6 28.9 |
| Grand Total | 100.0 |

TABLE 8.0

Fatty Acid Composition of Distillate (D2) (Example 7).

| Lipid Profiles | /% w/w |
|---|---|
| a C11 to a C19 | 11.6 |
| a C21 | 2.6 |
| a C23 to a C29 | 2.0 |
| Group Total n C10 to n C30 | 16.2 10.3 |
| Group Total i C10 to i C28 | 10.3 14.1 |
| Group Total C14 OH to C24 OH n C16 OH | 14.1 20.0 26.7 |
| Group Total Higher molecular Weight/Unknowns | 46.7 12.7 |
| Grand Total | 100.0 |

TABLE 9.0

Fatty Acid Composition of Residue (R2) (Example 7).

| Lipid Profiles | /% w/w |
|---|---|
| a C11 to a C19 | 0.5 |
| a C21 | 1.0 |
| a C23 to a C29 | 13.4 |

TABLE 9.0-continued

Fatty Acid Composition of Residue (R2) (Example 7).

| Lipid Profiles | /% w/w |
|---|---|
| Group Total n C10 to n C30 | 14.9 8.9 |
| Group Total i C10 to i C28 | 8.9 9.5 |
| Group Total C14 OH to C24 OH n C16 OH | 9.5 10.3 3.1 |
| Group Total Higher molecular Weight/Unknowns | 13.4 53.3 |
| Grand Total | 100.0 |

TABLE 10.0

Fatty Acid Composition of Distillate (D3) (Example 8).

| Lipid Profiles | /% w/w |
|---|---|
| a C11 to a C19 | 16.5 |
| a C21 | 5.2 |
| a C23 to a C29 | 4.6 |
| Group Total n C10 to n C30 | 26.3 22.7 |
| Group Total i C10 to i C28 | 22.7 35.5 |
| Group Total C14 OH to C24 OH n C16 OH | 35.5 3.5 3.7 |
| Group Total Higher molecular Weight/Unknowns | 7.2 8.3 |
| Grand Total | 100.0 |

TABLE 11.0

Fatty Acid Composition of Residue (R3) (Example 8).

| Lipid Profiles | /% w/w |
|---|---|
| a C11 to a C19 | 1.5 |
| a C21 | 2.3 |
| a C23 to a C29 | 23.9 |
| Group Total n C10 to n C30 | 27.7 17.1 |
| Group Total i C10 to i C28 | 17.1 18.6 |
| Group Total C14 OH to C24 OH n C16 OH | 18.6 1.3 0.7 |
| Group Total Higher molecular Weight/Unknowns | 2.0 34.6 |
| Grand Total | 100.0 |

TABLE 12.0

Fatty Acid Composition of The Distillate (D4) (Example 9).

| Lipid Profiles | /% w/w |
|---|---|
| a C11 to a C19 | 21.9 |
| a C21 | 1.5 |
| a C23 to a C29 | 0.1 |
| Group Total | 23.5 |
| n C10 to n C30 | 23.4 |
| Group Total | 23.4 |
| i C10 to i C28 | 37.7 |
| Group Total | 37.7 |
| C14 OH to C24 OH | 2.7 |
| n C16 OH | 3.5 |
| Group Total | 6.2 |
| Higher molecular Weight/Unknowns | 9.2 |
| Grand Total | 100.0 |

TABLE 13.0

Fatty Acid Composition of The Residue (R4) (Example 9).

| Lipid Profiles | /% w/w |
|---|---|
| a C11 to a C19 | 8.7 |
| a C21 | 10.6 |
| a C23 to a C29 | 11.4 |
| Group Total | 30.7 |
| n C10 to n C30 | 20.1 |
| Group Total | 20.1 |
| i C10 to i C28 | 29.4 |
| Group Total | 29.4 |
| C14 OH to C24 OH | 4.7 |
| n C16 OH | 3.7 |
| Group Total | 8.4 |
| Higher molecular Weight/Unknowns | 11.4 |
| Grand Total | 100.0 |

TABLE 14.0

Fatty Acid Composition of The Super-Refined Residue (R4) (Example 10).

| Lipid Profiles | /% w/w |
|---|---|
| a C11 to a C19 | 9.7 |
| a C21 | 12.3 |
| a C23 to a C29 | 12.1 |
| Group Total | 34.1 |
| n C10 to n C30 | 19.9 |
| Group Total | 19.9 |
| i C10 to i C28 | 33.5 |
| Group Total | 33.5 |
| C14 OH to C24 OH | 0.2 |
| n C16 OH | 0.5 |
| Group Total | 0.7 |
| Higher molecular Weight/Unknowns | 11.8 |
| Grand Total | 100.0 |

TABLE 15.0

Fatty Acid Composition of The Chromatographically Refined Distillate (D1) (Example 11).

| Lipid Profiles | /% w/w |
|---|---|
| a C11 to a C19 | 19.5 |
| a C21 | 4.7 |
| a C23 to a C29 | 10.6 |
| Group Total | 34.8 |
| n C10 to n C30 | 23.2 |
| Group Total | 23.2 |
| i C10 to i C28 | 32.3 |
| Group Total | 32.3 |
| C14 OH to C24 OH | 5.1 |
| n C16 OH | 2.3 |
| Group Total | 7.4 |
| Higher molecular Weight/Unknowns | 2.3 |
| Grand Total | 100.0 |

TABLE 16.0

Fatty Acid Composition of The Non-Clathratable Fatty Acids of Distillate (D1) (Example 12).

| Lipid Profiles | /% w/w |
|---|---|
| a C11 to a C19 | 28.0 |
| a C21 | 6.1 |
| a C23 to a C29 | 4.3 |
| Group Total | 38.4 |
| n C10 to n C30 | 12.4 |
| Group Total | 12.4 |
| i C10 to i C28 | 31.4 |
| Group Total | 31.4 |
| C14 OH to C24 OH | 3.1 |
| n C16 OH | 3.8 |
| Group Total | 6.9 |
| Higher molecular Weight/Unknowns | 10.9 |
| Grand Total | 100.0 |

TABLE 17.0

Fatty Acid Composition of The Clathratable Fatty Acids of Distillate (D1) (Example 12).

| Lipid Profiles | /% w/w |
|---|---|
| a C11 to a C19 | 5.7 |
| a C21 | 3.1 |
| a C23 to a C29 | 20.8 |

TABLE 17.0-continued

Fatty Acid Composition of The Clathratable Fatty Acids of Distillate (D1) (Example 12).

| Lipid Profiles | /% w/w |
| --- | --- |
| Group Total | 29.6 |
| n C10 to n C30 | 21.9 |
| Group Total | 21.9 |
| i C10 to i C28 | 28.2 |
| Group Total | 28.2 |
| C14 OH to C24 OH | 0.6 |
| n C16 OH | 0.8 |
| Group Total | 1.4 |
| Higher molecular Weight/Unknowns | 18.9 |
| Grand Total | 100.0 |

TABLE 18.0

Fatty Acid Composition of The Non-Clathratable Fatty Acids of Distillate (D1) (Example 13).

| Lipid Profiles | /% w/w |
| --- | --- |
| a C11 to a C19 | 23.4 |
| a C21 | 5.7 |
| a C23 to a C29 | 8.8 |
| Group Total | 37.9 |
| n C10 to n C30 | 15.1 |
| Group Total | 15.1 |
| i C10 to i C28 | 29.7 |
| Group Total | 29.7 |
| C14 OH to C24 OH | 2.7 |
| n C16 OH | 3.2 |
| Group Total | 5.9 |
| Higher molecular Weight/Unknowns | 11.4 |
| Grand Total | 100.0 |

TABLE 19.0

Fatty Acid Composition of The Clathratable Fatty Acids of Distillate (D1) (Example 13).

| Lipid Profiles | /% w/w |
| --- | --- |
| a C11 to a C19 | 6.2 |
| a C21 | 2.4 |
| a C23 to a C29 | 16.5 |
| Group Total | 25.1 |
| n C10 to n C30 | 24.3 |
| Group Total | 24.3 |
| i C10 to i C28 | 28.0 |
| Group Total | 28.0 |
| C14 OH to C24 OH | 0.9 |
| n C16 OH | 0.8 |

TABLE 19.0-continued

Fatty Acid Composition of The Clathratable Fatty Acids of Distillate (D1) (Example 13).

| Lipid Profiles | /% w/w |
| --- | --- |
| Group Total | 1.7 |
| Higher molecular Weight/Unknowns | 19.9 |
| Grand Total | 100.0 |

TABLE 20.0

Fatty Acid Composition of The Non-Clathratable Fatty Acids of Distillate (D1) (Example 14).

| Lipid Profiles | /% w/w |
| --- | --- |
| a C11 to a C19 | 21.5 |
| a C21 | 5.3 |
| a C23 to a C29 | 9.2 |
| Group Total | 36.0 |
| n C10 to n C30 | 16.1 |
| Group Total | 16.1 |
| i C10 to i C28 | 29.0 |
| Group Total | 29.0 |
| C14 OH to C24 OH | 2.5 |
| n C16 OH | 2.8 |
| Group Total | 5.3 |
| Higher molecular Weight/Unknowns | 13.6 |
| Grand Total | 100.0 |

TABLE 21.0

Fatty Acid Composition of The Clathratable Fatty Acids of Distillate (D1) (Example 14)

| Lipid Profiles | /% w/w |
| --- | --- |
| a C11 to a C19 | 13.2 |
| a C21 | 3.5 |
| a C23 to a C29 | 17.2 |
| Group Total | 33.9 |
| n C10 to n C30 | 26.4 |
| Group Total | 26.4 |
| i C10 to i C28 | 28.3 |
| Group Total | 28.3 |
| C14 OH to C24 OH | 1.7 |
| n C16 OH | 1.8 |
| Group Total | 3.5 |
| Higher molecular Weight/Unknowns | 7.9 |
| Grand Total | 100.0 |

Notes:
a: ante-iso, i: iso, n: normal OH: 2-hydroxy, fatty acids

Water Phase

| | |
| --- | --- |
| Glycerin (Croderol GV9000) (1) | 4 wt % |
| Triethanolamine | to pH 4.0 |

| | |
|---|---|
| Deionised water | to 100 wt % |
| Perfume, Preservative, Colour | qs |

(1) Supplied by Croda Chemicals

The oil and water phase ingredients, except the perfume, were prepared separately at between 65° and 70° C. with stirring. The water phase ingredients, except the perfume, were added to the oil phase whilst maintaining the temperature and stirring action. The perfume was added with stirring to the mixture when the cream had cooled to below 45° C. and the pH was adjusted to 4.0.

From the foregoing, it can therefore be seen that the present invention provides a process for preparing 18-methyl eicosanoic acid (18-MEA) and/or an ahpha-hydroxy acid (AHA), which process comprises:
  (a) heating to 100 to 230° C. woolwax acids or a derivative thereof that forms an estolide and/or polymer thereof under process conditions;
  (b) distilling the estolides and/or polymers resulting from step (a); and, optionally,
  (c) further processing the distillate (D1) and/or the residue (R1) resulting from step (b).

Such further processing may comprise further distillation to produce a second or subsequent distillate and residue, D3 and R3 in the case of direct re-distillation of D1, followed by D4 and R4, or D2 after saponification and hydrolysis by a saponifying and hydrolysing agent of R1; which distillates and residues may be further purified by one or more of inclusion complexation and/or chromatography, as described in more detail hereinbefore.

Particular derivatives of woolwax acids that may be used in the process are esters thereof, such as straight or branched chain alkyl esters, for example, wherein the alkyl group has from 1 to 10, such as 1 to 6, preferably 1 to 4 carbon atoms. Suitable examples of such derivatives are therefore are methyl, ethyl or propyl esters of a woolwax fatty acid, or a formate or acetate of an AHA.

The present invention therefore further provides a compound selected from the group consisting of 18-MEA and AHAs whenever produced by a process according to the invention. Particularly preferred compounds are those such as 18-MEA and alpha-hydroxy acids having from 8 to 30, more preferably, 14 to 26, carbon atoms, such as alpha-hydroxy palmitic acid.

In view of the previously-mentioned uses to which the 18-MEA and AHAs may be put, the present invention further provides a cosmetic product or emollient comprising a compound prepared according to the process of the invaiton, preferably in a form suitable for application to the hair or skin. Therefore the invention still further provides a method for the treatment of hair or skin, which method comprises administration to the hair or skin of a compound prepared according to the process of the invention.

What we claim is:

1. A process for preparing an acid selected from 18-methyl eicosanoic acid (18-MEA) and an alpha-hydroxy acid (AHA), and mixtures thereof, comprising:
  (a) distilling a species selected from estolides and polymers obtainable by heating to 100° to 230° C. woolwax acids or a derivative thereof to produce a product selected from a distillate (D1) and a residue (R1); and
  (b) saponifying and then hydrolysing the species-rich residue (R1) to recover AHAs.

2. A process according to claim 1, wherein the woolwax acids or derivative thereof is heated to 150° to 200° C.

3. A process according to claim 1, wherein the woolwax acids or derivative thereof is heated to 160° to 180° C.

4. A process according to claim 1, wherein the woolwax acids or derivative thereof is heated for a period of from 1 to 48 hours.

5. A process according to claim 1, wherein the woolwax acids or derivative thereof is heated for a period of 5 to 10 hours.

6. A process according to claim 1, wherein the step of heating the woolwax acids or derivative thereof is carried out under vacuum.

7. A process according to claim 1, the step of heating the woolwax acids or derivative thereof is carried out in presence of a catalyst.

8. A process according to claim 1, wherein the distillation directly follows preparation of the estolide and/or polymer.

9. A process according to according to claim 1, wherein the distillation is carried out as a separate stage from the preparation of the estolide and/or polymer.

10. A process according to claim 1, wherein the distillation step is carried out at between 150° and 250° C.

11. A process according to claim 1, wherein the saponification step is carried out by an aqueous alcoholic solution of a base.

12. A process according to claim 1, wherein 18-MEA is obtained from the distillate (D1) by at least one technique selected from the group consisting of (1) further distillation thereof to give a distillate (D3) and a residue (R3); (2) by chromatographic refining; and (3) by using a combination of distillation and chromatographic refining.

13. A process for preparing an acid selected from 18-methyl eicosanoic acid (18-MEA) and an alpha-hydroxy acid (AHA), and mixtures thereof, comprising:
  (a) heating to 100° to 230° C. woolwax acids or a derivative thereof to form a species selected from estolides and polymers thereof under process conditions;
  (b) distilling the species resulting from step (a);
  (c) saponifiying and hydrolysing the species-rich residue (R1) resulting from step (b) to recover AHAs, and,
  (d) optionally, further processing the distillate (D1) resulting from step (b) and/or the saponified and hydrolysed residue (R1).

14. A process according to claim 13, wherein the woolwax acids or derivative thereof is heated to 150° to 200° C.

15. A process according to claim 13, wherein the woolwax acids or derivative thereof is heated to 160° to 180° C.

16. A process according to claim 13, wherein the woolwax acids or derivative thereof is heated for a period of from 1 to 48 hours.

17. A process according to claim 13, wherein the woolwax acids or derivative thereof are heated for a period of 5 to 10 hours.

18. A process according to claim 13, wherein the step of heating the woolwax acids or derivative thereof is carried out under vacuum.

19. A process according to claim 13, the step of heating the woolwax acids or derivative thereof is carried out in the presence of a catalyst.

20. A process according to claim 13, wherein the distillation directly follows preparation of the estolide and/or polymer.

21. A process according to according to claim 13, wherein the distillation is carried out as a separate stage from the preparation of the estolide and/or polymer.

22. A process according to claim 13, wherein the distillation step is carried out at between 150° and 250° C.

23. A process according to claim 13, wherein the saponification step is carried out by an aqueous alcoholic solution of a base.

24. A process according to claim 23, wherein the hydrolysis step is carried out by a strong acid.

25. A process according to claim 24, wherein the AHAs are further distilled to give a distillate (D2) and a residue (R2).

26. A process according to claim 25, wherein the distillation temperature is from 100° to 230° C.

27. A process according to claim 25 wherein the distillation temperature is from 120° to 180° C.

28. A process according to claim 13, wherein 18-MEA is obtained from the distillate (D1) by at least one technique selected from the group consisting of (1) further distillation thereof to give a distillate (D3) and a residue (R3); (2) by chromatographic refining; and (3) by using a combination of distillation and chromatographic refining.

29. A process according to claim 28, wherein the distillation temperature is from 100° to 230° C.

30. A process according to claim 28, wherein the distillation temperature is from 120° to 180° C.

31. A process according to claim 28, wherein the distillate (D3) is further distilled to give a distillate (D4) and a residue (R4).

32. A process according to claim 31, wherein the distillation temperature is from 80° to 230° C.

33. A process according to claim 31, wherein the distillation temperature is from 105° to 160° C.

34. A process according to claim 13, wherein the distillation step is carried out under vacuum.

35. A process according to claim 34, wherein the vacuum is $1 \times 10^{-1}$ mbar.

36. A process according to claim 34, wherein the vacuum is $1 \times 10^{-2}$ mbar.

37. A process according to claim 13, wherein the 18-MEA in D1, D3 or R4 is further chromatographically refined.

38. A process according to claim 13, wherein the distillate (D1 or D3) and/or residue (R4) are further purified by an inclusion complexation step.

39. A process according to claim 38, further comprising using urea as an inclusion complex forming agent the inclusion complexation step.

40. A process according to claim 13, wherein the woolwax acids are obtained from saponification of woolwax.

41. A process according to claim 13, wherein the derivatives of woolwax acids are esters including the acid functionality of the woolwax and/or esters including the hydroxyl functionality of the AHAs.

42. A process according to claim 41, wherein the derivatives are methyl, ethyl or propyl esters of a woolwax fatty acid, or a formate or acetate of an AHA.

* * * * *